United States Patent [19]

Rose et al.

[11] 4,129,413

[45] Dec. 12, 1978

[54] OXIDATION HAIR DYES BASED UPON TETRAAMINOPYRIMIDINE DEVELOPERS AND MONO- AND DIALKYL -M-DIHYDROXY BENZENE COUPLERS

[75] Inventors: David Rose, Hilden; Erwin Weinrich, Haan; Edgar Lieske, Düsseldorf, all of Fed. Rep. of Germany

[73] Assignee: Henkel Kommanditgesellschaft auf Aktien (Henkel KGaA), Düsseldorf, Fed. Rep. of Germany

[21] Appl. No.: 787,465

[22] Filed: Apr. 14, 1977

[30] Foreign Application Priority Data

Apr. 23, 1976 [DE] Fed. Rep. of Germany ....... 2617739

[51] Int. Cl.² .......................... A61K 7/13; D06P 1/32
[52] U.S. Cl. ............................................ 8/10.2; 8/11
[58] Field of Search ..................................... 8/10.2, 11

[56] References Cited

U.S. PATENT DOCUMENTS 4,003,699  1/1977  Rose et al. ............................. 8/10.2

*Primary Examiner*—Sam Rosen
*Attorney, Agent, or Firm*—Hammond & Littell

[57] ABSTRACT

An aqueous hair dye preparation comprising an oxidation dyestuff combination of a developer component consisting of a tetraaminopyrimidine derivative or a water-soluble acid addition salt thereof and a coupler component consisting of a mono- and/or dialkyl-m-dihydroxybenzene, wherein the alkyl radical has 1–4 carbon atoms; as well as a process for dyeing hair by utilizing this oxidation dyestuff combination.

16 Claims, No Drawings

OXIDATION HAIR DYES BASED UPON TETRAAMINOPYRIMIDINE DEVELOPERS AND MONO- AND DIALKYL -M- DIHYDROXY BENZENE COUPLERS

THE PRIOR ART

Of great importance for the dyeing of hair are the so-called oxidation dyestuffs because of their intensive colors and very good fastness. These dyestuffs are formed by the oxidative coupling of a developer component with a coupling component. The developers customarily used are nitrogenous bases, such as p-phenylenediamine derivatives, diaminopyridines, 4-aminopyrazolone derivatives or heterocyclic hydrazones. Useful as so-called coupling components are m-phenylenediamine derivatives, phenols, naphthols, resorcinol derivatives and pyrazolones.

Good oxidation dyestuff components for hair dyeing must fulfill all of the following requirements.

They have to be able to develop a sufficient intensity of the desired color shades when oxidatively coupled with the respective developer component or coupling component. Furthermore, they have to possess a capacity for being absorbed by human hair, which capacity ranges from sufficient to very good; and in addition, they should be unobjectionable from toxicological and dermatological viewpoints.

As developers, it is customary to use the class of compounds consisting of substituted or unsubstituted p-phenylenediamines. However, this class of compounds has the disadvantage that sensitivity reactions and subsequently severe allergies are caused in numerous persons. The developers which have been recently proposed for avoiding these dermatological disadvantages are not always fully satisfactory with respect to their technical application.

U.S. Pat. No. 4,003,699, Jan. 18, 1977, discloses oxidation hair dyes based upon tetraaminopyrimidine developers which can react with the known couplers generally used in oxidation hair dyestuffs to give very intensive, varying shades which previously could not be obtained with these known couplers. U.S. Pat. No. 4,003,699 also discloses the special usefulness of its tetraaminopyrimidines employed as developers in combination with certain m-aminophenols as blue-coupling components.

It is further disclosed in the above patent that the tetraaminopyrimidines disclosed therein are characterized by very good fastness of the dyeings produced with them, good water solubility, good storage stability, and toxicological and dermatological harmlessness.

While the tetraaminopyrimidine developers of the above patent are shown therein to be especially useful in combination with certain known couplers in providing oxidation hair dyes, there are nevertheless special requirements for hair dyes which cannot be met by generally known developer/coupler combinations. For example, in order to obtain intensive color tones which come as closely as possible to natural hair shades, a full-value red dye is very important as a shading component. The preparation of such a red dye with the use of the otherwise highly satisfactory tetraaminopyrimidines as developer substances presents difficulties, which are due to the lack of suitability of the conventional coupler components. For example, resorcinol, which has generally been used heretofore as a red coupler component, yields in combination with tetraaminopyrimidine a dye which leaves much to be desired in terms of fastness to light and penetrating power.

A need therefore existed to find a developer/coupler combination which yields red dyes, which meet all the requirements of fastness, stability, and toxicological and dermatological harmlessness desirable in oxidation hair dyes, and which lead beyond this to strong and natural hair shades.

OBJECTS OF THE INVENTION

An object of the invention is to provide usable oxidation hair dyes containing suitable components which optimally satisfy the above requirements.

Another object of the present invention is to provide an oxidation dyestuff combination of a developer component and a coupling component, which is based on tetraaminopyrimidines as the developer component and mono- and/or dialkyl-m-dihydroxybenzenes as the coupler component.

These and further objects of the present invention will become apparent as the description thereof proceeds.

DESCRIPTION OF THE INVENTION

The present invention provides a composition and process for dyeing hair based upon an oxidation dyestuff combination of a developer component which is a tetraaminopyrimidine and a coupling component which is a mono- and/or dialkyl-m-dihydroxybenzene. It has now been found that the above-specified requirements can be fulfilled to an especially significant extent by the use of hair coloring preparations that are based on oxidation dyestuff combinations containing tetraaminopyrimidines of the formula

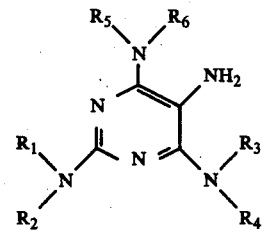

and their inorganic or organic water-soluble acid addition salts as developers, in which $R_1$ to $R_6$ are each selected from the group consisting of hydrogen, alkyl having 1 to 4 carbon atoms, aryl, substituted aryl and $-(CH_2)_n-X$, in which n is an integer from 1 to 4, and X is selected from the group consisting of hydroxy, halogen and $-NR_7R_8$ wherein $R_7$ and $R_8$ are selected from the group consisting of hydrogen and alkyl having 1 to 4 carbon atoms and can form with the nitrogen atom a heterocyclic ring which may contain one additional nitrogen atom or an oxygen atom, and in which $R_1$ to $R_6$ likewise can designate an optionally substituted five-membered or six-membered heterocyclic ring containing one or two nitrogen atoms, or one nitrogen atom and one oxygen atom, and containing mono- and/or dialkyl-m-dihydroxy-benzenes as couplers, in which the alkyl radicals have 1 to 4 carbon atoms.

More particularly, the present invention is directed to an aqueous preparation for the dyeing of hair consisting essentially of (1) from 0.2% to 5% by weight of an oxidation dyestuff combination of a developer component, and a coupling component in substantially equimolar amounts, said developer component consisting essentially of (A) a tetraaminopyrimidine of the formula

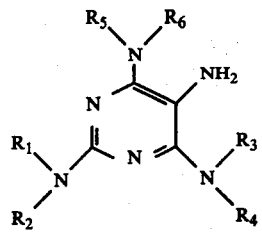

wherein R₁, R₂, R₃, R₄, R₅ and R₆ are each selected from the group consisting of hydrogen, phenyl, alkyl having 1 to 4 carbon atoms, phenylalkyl having 7 to 10 carbon atoms, phenylalkenyl having 7 to 10 carbon atoms, $$X-(CH_2)_n-$$

wherein n is an integer from 1 to 4, and X is selected from the group consisting of hydroxyl, halogen and NR₇R₈— in which R₇ and R₈ are each hydrogen or alkyl having 1 to 4 carbon atoms, and together with the nitrogen atom R₇ and R₈ form a member selected from the group consisting of a 5 to 6 membered heterocyclic ring optionally containing an additional nitrogen atom or oxygen atom, and wherein R₁ and R₂, or R₃ and R₄, or R₅ and R₆, together with the nitrogen atom form a five to six membered heterocyclic ring optionally containing another nitrogen or oxygen atom in the ring and (B) a water-soluble acid addition salt of (A), and said coupler component consisting essentially of a mono- and/or di-alkyl-m-dihydroxybenzene; (2) from 0% to 5% by weight of a direct dyestuff; (3) from 0% to 30% by weight of a surfactant; (4) from 0% to 25% by weight of thickeners; and (5) the balance up to 100% by weight of water.

A particularly preferred subgenus of the above-mentioned developer component is wherein R₁, R₂, R₃, R₄, R₅ and R₆ are each selected from the group consisting of hydrogen, methyl, ethyl, isopropyl, n-propyl, butyl, phenyl, benzyl and benzylidene, or —(CH₂)ₙ—X, and wherein R₁ and R₂, or R₃ and R₄, or R₅ and R₆, together with the nitrogen atom form a substituent selected from the group consisting of piperidino and morpholino; and wherein n is 1, 2 or 3 and X is selected from the group consisting of hydroxyl, halogen and —NR₇R₈ in which R₇ and R₈ are each hydrogen or alkyl having 1 to 4 carbon atoms.

The above tetraaminopyrimidines are disclosed in U.S. Pat. No. 4,003,699, the teachings of which are incorporated herein by reference.

The tetraaminopyrimidines which are to be used as developer components according to the invention can be used either as such or in form of their water-soluble acid addition salts with non-toxic inorganic acids or organic acids, such as for example, hydrochloric acid, sulfuric acid, phosphoric acid, acetic acid, propionic acid, lactic acid or citric acid.

The preparation of most tetraaminopyrimidines to be used as developer components according to the invention is already known in the literature and can be taken from the monograph by D. J. Brown, in the series "Heterocyclic Compounds", Interscience Publishers, 1962, Vols. I and II, "The Pyrmidines". The preparation of some of the tetraaminopyrimidines of the invention is disclosed in U.S. Pat. No. 4,003,699.

To synthesize the tetraaminopyrimidine compounds to be used according to the invention, the starting material generally is a 2,4,6-aminopyrimidine, into which the 5-amino group is introduced by nitrosation and subsequent reduction. It is also possible to start from the corresponding substituted triaminoalkylmercaptopyrimidines and to replace the alkylmercapto group with an amino group. The latter method is especially suitable for the introduction of substituted amino groups into the 2-, 4-, or 6-positions of the pyrimidine ring. Suitable examples of developer components to be used according to the invention, are for example: 2,4,5,6-tetraamino-pyrimidine, 4,5-diamino-2,6-bis(methylamino)-pyrimidine, 2,5-diamino-4,6-bis-(methylamino)-pyrimidine, 4,5-diamino-6-(butylamino)-2-(dimethylamino)-pyrimidine, 2,5-diamino-4-(diethylamino)-6-(methylamino)-pyrimidine, 4 5-diamino-6-(diethylamino)-(2-dimethylamino)-pyrimidine, 4,5-diamino-2-(diethylamino)-6-(methylamino)-pyrimidine, 4,5-diamino-2-(dimethylamino)-6-(ethylamino)-pyrimidine, 4,5-diamino-2-(dimethylamino)-6-(isopropylamino)-pyrimidine, 4,5 diamino-2-(dimethylamino)-6-(methylamino)-pyrimidine, 4,5-diamino-6-(dimethylamino)-2-(methylamino)-pyrimidine, 4,5-diamino-2-(dimethylamino)-6-(propylamino)-pyrimidine, 2,4,5-triamino-6-(dimethylamino)-pyrimidine, 4,5,6-triamino-2-(dimethylamino)-pyrimidine, 2,4,5-triamino-6-(methylamino)-pyrimidine, 4,5,6-triamino-2-(methylamino)-pyrimidine, 4,5-diamino-2-(dimethylamino)-6-piperidinopyrimidine, 4,5-diamino-6-(methylamino)-2-piperidino-pyrimidine, 2,4,5-triamino-6-piperidino-pyrimidine, 2,4,5-triamino-6-anilino-pyrimidine, 2,4,5-triamino-6-(benzylamino)-pyrimidine, 2,4,5-triamino-6-(benzylideneamino)-pyrimidine, 4,5,6-triamino-2-piperidino-pyrimidine, 5-amino-2,4,6-tris-(methylamino)pyrimidine, 2,4,5-triamino-6-(di-n-propylamino)pyrimidine, 2,4,5-triamino-6-morpholino-pyrimidine, 2,5,6-triamino-4-(dimethylamino)-pyrimidine, 4,5,6-triamino-2-morpholino-pyrimidine, 2,4,5-triamino-6-(β-hydroxyethyl-amino)pyrimidine, 4,5,6-triamino-2-[(β-aminoethyl)amino]-pyrimidine, 2,5,6-triamino-4-[(β-methylamino)-ethylamino] pyrimidine, 2,5-diamino-4,6 [bis-(γ-diethylamino)-propylamino]-pyrimidine, 4,5-diamino-6-[(B-hydroxyethyl)-amino]-2-(methylamino)pyrimidine, 5-amino-2,4,6-(triethylamino)-pyrimidine, and 5-amino-6-anilino-2,4-[bis-(β-hydroxyethyl)-amino]-pyrimidine.

According to the invention, the tetraaminopyrimidines as developers are used in combination with coupler compounds which are monoalkyl-m-dihydroxybenzenes or dialkyl-m-dihydroxybenzenes or any combination of said dihydroxybenzenes, wherein the alkyl radicals have 1-4 carbon atoms. These coupler components yield in combination with the tetraaminopyrimidines of the invention red dyes, which meet all the requirements of such dyes with respect to fastness, stability, toxicological and dermatological harmlessness, and which also read to strong and natural hair shades.

The m-dihydroxybenzene couplers have the formula

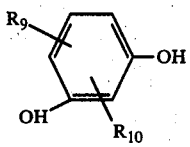

wherein $R_9$ is a member selected from the group consisting of hydrogen and alkyl having from 1 to 4 carbon atoms and $R_{10}$ is alkyl having from 1 to 4 carbon atoms.

Suitable examples of red coupler substances to be used according to the invention are: 2,6-dihydroxytoluene, 2,4-dihydroxytoluene, 3,5-dihydroxytoluene, 2,6-dihydroxyethylbenzene, 2,4-dihydroxyethylbenzene, 3,5-dihydroxyethylbenzene, 2,6-dihydroxypropylbenzene, 2,4-dihydroxypropylbenzene, 3,5-dihydroxypropylbenzene, 2,6-dihydroxyisopropylbenzene, 2,4-dihydroxyisopropylbenzene, 3,5-dihydroxyisopropylbenzene, 2,6-dihydroxybutylbenzene, 2,4-dihydroxybutylbenzene, 3,5-dihydroxybutylbenzene, 2,4-dimethyl-1,3-dihydroxybenzene, 2,4-diethyl-1,3-dihydroxybenzene, 2,4-diisopropyl-1,3-dihydroxybenzene, 2,4-dibutyl-1,3-dihydroxybenzene, 2,3-dimethyl-1,5-dihydroxybenzene, 2,3-diethyl-1,5-dihydroxybenzene, 2,3-dipropyl-1,5-dihydroxybenzene, 2,4-dimethyl-1,5-dihydroxybenzene, 2,4-diethyl-1,5-dihydroxybenzene, 2,4-dibutyl-1,5-dihydroxybenzene, 2,5-dimethyl-1,3-dihydroxybenzene, 2,5-diethyl-1,3-dihydroxybenzene, 2,5-diisopropyl-1,3-dihydroxybenzene, and 2,5-dibutyl-1,3-dihydroxybenzene.

Particularly preferred are the mono- and di-methyl-m-dihydroxybenzenes, both in terms of their application as red coupler components and their easy accessibility.

The monoalkyl, in particular the monomethyl, -m-dihydroxybenzenes yield in combination with the tetraaminopyrimidines especially advantageous red dyes of varying suitable shadings. Examples of such particularly effective red couplers are 2,6-dihydroxytoluene, 3,5-dihydroxytoluene, 2,4-dihydroxytoluene, and 2,6-dihydroxyethylbenzene.

The mono- and/or di-alkyl-m-dihydroxybenzenes to be used according to the invention are known in the literature, and they are easily prepared according to generally known methods.

In the hair coloring preparations according to the invention, the coupler substances are generally used in substantially equimolar amounts, relative to the developer substances used. Although an equimolar amount is preferred, it is possible to use more or less of either component in the molar range of 2:1 to 1:2, such as e.g. up to a 10% excess or deficiency.

Furthermore, the developer component and the coupling component may be used as pure ingredients or as mixtures. Not only can the developer component consist of mixtures of the tetraaminopyrimidines to be used according to the invention, but the coupler substance can also consist of mixtures of the above-mentioned mono- and/or dialkyl-m-dihydroxybenzenes.

In addition, the hair coloring preparations according to the invention can contain admixtures of other customary developing components. Besides developer and-/or coupler components they can, if necessary, also contain the customary direct dyestuffs in case the latter are needed for obtaining certain shades. From 0% to 5% direct dyestuffs may be employed. Some examples of such other customary developers are p-phenylene diamine derivatives, diaminopyridines, 4-aminopyrazolone derivatives and heterocyclic hydrazones. Some examples of such other customary couplers are m-phenylene diamine derivatives, phenols, naphthols, resorcinol derivatives and pyrazolones. Besides these, yet other such conventional developers and couplers will be readily perceived by those skilled in the art. As in the case of other oxidation hair dyes, the oxidative coupling, i.e., the developing of the dye can in principle be effected by atmospheric oxygen. However, it is preferred to use chemical oxidizing agents. Suitable examples are especially hydrogen peroxide or its products of addition to urea, melamine and sodium borate, as well as mixtures of such hydrogen peroxide addition products with potassium peroxydisulfate.

As developer components the tetraaminopyrimidines according to the invention have the advantage that they readily yield satisfactory hair dyeing results in oxidative coupling with atmospheric oxygen. Thus hair damage by the oxidizing agents, otherwise used in oxidative coupling, can be avoided. But if a brightening or bleaching effect is desired in the hair, in addition to the coloring effect, then the concurrent use of chemical oxidizing agents is necessary.

For the application, the hair dyes according to the invention are incorporated into suitable aqueous cosmetic preparations, such as creams, emulsions, gels or simple solutions and immediately before application to the hair, one of the above-named oxidizing agents is added. These hair dyeing preparations contain coupling and developing components in amounts of from 0.2% to 5% by weight, preferably from 1% to 3% by weight.

For the preparation of creams, emulsions or gels, the dye components are mixed with the additional ingredients customarily used in such preparations. Such additional ingredients are, for example, wetting agents or emulsifiers of the anionic or nonionic type, such as alkylbenzenesulfonates, higher fatty alcohol sulfates, higher alkylsulfonates, higher fatty acid alkanolamides, addition products of ethylene oxide on higher fatty alcohols, thickeners, such as methyl cellulose, starch, higher fatty alcohols, paraffin oil and higher fatty acids. Furthermore, perfumes and hair-conditioning and grooming agents, such as pantothenic acid and cholesterol may be included.

Effective amounts of the above-named additives are those customarily employed for this purpose. For example, effective amounts of wetting agents and emulsifiers range from 0.5% to 30% by weight, preferably from 1% to 15% by weight; and for thickeners, an effective amount ranges from 0.1% to 25% by weight, preferably from 1% to 15% by weight, based in each case on the total weight of the preparation. As a lower limit for the above additives, a zero percent lower limit is possible, if none of the additive is utilized.

The hair coloring preparations according to the invention can be applied in a weakly acid medium, a neutral medium or especially in an alkaline medium, preferably at a pH of 8 to 10, regardless of whether a solution, an emulsion, a cream, or a gel is employed.

These preparations are applied at a temperature which usually ranges from 15° C. to 40° C. and preferably is room temperature.

After the preparation has been allowed to react for about 30 minutes, the hair coloring preparation is removed from the hair to be dyed, by rinsing. Then the hair is washed with a mild shampoo, and finally is dried.

The mono- and di-alkyl-m-dihydroxybenzenes used as coupler substances according to the invention yield in combination with the tetraaminopyrimidine developers very intensive red to red-brown color shades, which could not be achieved with these developers and conventional couplers, and they therefore represent a substantial enrichment in oxidative hair dyeing possibilities. The red dyes obtained are furthermore characterized by good fastness to light and penetrating power.

The following examples are merely illustrative of the present invention without being deemed limitative in any manner thereof.

EXAMPLES

In the following examples, the following mono- and di-alkyl-m-dihydroxy-benzenes were used as coupler components:

Product A: 2,6-dihydroxytoluene
Product B: 3,5-dihydroxytoluene
Product C: 2,4-dihydroxytoluene
Product D: 2,6-dihydroxyethylbenzene
Product E: 4,5-dimethyl-1,3-dihydroxybenzene They were combined with the following developer components in the hair dyes according to the invention:

Product I: 2,4,5,6-tetraaminopyrimidine
Product II: 2-methylamino-4,5,6-triaminopyrimidine
Product III: 2-dimethylamino-4,5,6-triaminopyrimidine
Product IV: 2,6-bis-dimethylamino-4,5-diaminopyrimidine
Product V: 4-piperidino-2,5,6-triaminopyrimidine
Product VI: 2-morpholino-4,5,6-triaminopyrimidine

EXAMPLE 1

The hair dyes according to the invention were used in the form of a cream emulsion. The emulsion contained 10 parts by weight of fatty alcohols having 12 to 18 carbon atoms, 10 parts by weight of fatty alcohol sulfate (sodium salt) having 12 to 18 carbon atoms and 75 parts by weight of water.

Into each emulsion, there was incorporated 0.01 mole of the tetraaminopyrimidines and 0.01 mole of the mono- or di-alkyl-m-dihydroxybenzenes which are listed in the following Table 1. Then, the pH-value of the emulsion was adjusted with ammonia to 9.5, and the emulsion was made up to 100 parts by weight with water. The oxidative coupling was effected by using as an oxidizing agent either atmospheric oxygen, or a 1% hydrogen peroxide solution, with the proviso that 10 parts by weight of hydrogen peroxide solution were added to 100 parts by weight of the emulsion. The respective dyeing cream, with or without additional oxidizing agents, was applied to human hair that was 90% gray and that had not been pretreated in a special manner. After the cream had remained on the hair for 30 minutes to complete the dyeing process, the hair was washed with a customary shampoo and then dried. The shades thereby obtained are also listed in the following Table 1.

TABLE I

| Ex. | Developer | Coupler | Shade Obtained With Atmospheric Oxygen | With 1% H$_2$O$_2$ Solution |
|---|---|---|---|---|
| 2 | Product I | Product A | Red brown | Red brown |
| 3 | " I | " B | Brick red | Reddish brown |
| 4 | " I | " C | Light brown | Light brown |
| 5 | " I | " D | Red | Red |
| 6 | " I | " E | Brown red | Brown red |
| 7 | " II | " A | Violet brown | Violet brown |
| 8 | " II | " B | Red brown | Red brown |
| 9 | " III | " A | Red | Red |
| 10 | " III | " B | Raspberry red | Brown red |
| 11 | " III | " C | Red brown | Red brown |
| 12 | " IV | " A | Brown | Red brown |
| 13 | " IV | " B | Red brown | Light brown |
| 14 | " IV | " C | Brown-orange | Brown-orange |
| 15 | " V | " A | Brown | Brown |
| 16 | " V | " B | Brown | Brown |
| 17 | " VI | " A | Gray-ruby | Gray-ruby |
| 18 | " VI | " B | Red brown | Red brown |
| 19 | " VI | " C | Light brown | Light brown |
| 20 | " VI | " E | Brown red | Red brown |

In order to demonstrate the considerable improvement in results obtained using the hair dyes according to the invention with respect to fastness to light and penetrating power, comparison dyeings were made in accordance with the procedures of Example 1 above, using in one case 4-methylresorcinol (2,4-dihydroxytoluene) as the red coupler component according to the invention, and in another case resorcinol as a conventional red coupler component. 2,4,5,6 tetraaminopyrimidine was used as the developer component in both cases.

EXAMPLE 21

FASTNESS TO LIGHT

The fastness to light was determined according to DIN 54,004("Determination of the fastness to light of dyeings and prints with artificial daylight"). The dyed hair samples together with the eight dyeings of a light fastness standard were exposed to xenon arc light. The fastness was evaluated by comparing the bleaching of the dyed hair samples with the bleaching of the types of the light fastness standard. Grade 1 denotes a very low, and grade 8 a very high fastness to light. The light fastness standard is obtained using the following dyes on smooth wool material with a weight per unit area of 200 g/m$^2$.

| LIGHT FASTNESS STANDARD | |
|---|---|
| Type of light fastness | Dye color index designation |
| 1 | CJ Acid Blue 104 |
| 2 | CJ Acid Blue 109 |
| 3 | CJ Acid Blue 83 |
| 4 | CJ Acid Blue 121 |
| 5 | CJ Acid Blue 47 |
| 6 | CJ Acid Blue 23 |
| 7 | CJ Solubilized Vat Blue 5 |
| 8 | CJ Solubilized Vat Blue 8 |

A xenon arc lamp with a color temperature of 5500°–6500° K., whose ultraviolet radiation is reduced by a window glass filter, was used as the light source.

The samples of the dyed hair and of the light fastness standard were secured on a cardboard side by side and provided with a covering templet, which covers the edge zones of the samples parallel to the longitudinal edge of the sample holder. Then the samples were exposed to the light source until light fastness type 3 showed a noticeable color difference between the exposed and the unexposed part.

It was then determined whether the dyed hair samples showed changes, and these were evaluated in comparison to the changes in types 1, 2 and 3 of the light fastness standard. The exposure was then continued until light fastness type 4 showed a noticeable color difference between the exposed and the unexposed part. Thus, after changing the templet, the exposure was continued until color changes in the same were perceived.

The light fastness measurements effected in the above way yielded for the hair dye based on resorcinol a fastness value of 3 and for the dye based on 4-methylresorcinol a fastness value of 4. This means that a color change in the hair dye according to the invention takes place only after double the exposure time required to bring about the color change in the comparison hair dye.

EXAMPLE 22

PENETRATING POWER

In order to determine penetrating power, correspondingly dyed locks of hair using the coupler of the invention and the conventional coupler were embedded in polyester casting resin. Microsections were made of the embedded hair and examined under the microscope. It was found that the hair dye based on resorcinol yields a strong dyeing of the hair on the edge, but only weak penetration. But the hair dyed with the hair dye based on 4-methylresorcinol showed a complete and strong penetration.

We claim:

1. A composition of the developer-coupler type for the dyeing of hair, consisting essentially of, as developer, (A) a tetraaminopyrimidine of the formula

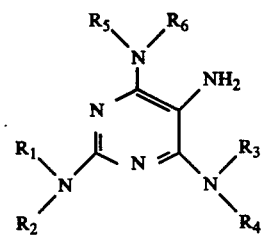

wherein $R_1$, $R_2$, $R_3$, $R_4$, $R_5$ and $R_6$ are each selected from the group consisting of hydrogen, phenyl, alkyl having 1 to 4 carbon atoms, phenylalkyl having 7 to 10 carbon atoms, phenylalkenyl having 7 to 10 carbon atoms, $$X-(CH_2)_n-$$

wherein n is an integer from 1 to 4, and X is selected from the group consisting of hydroxyl, halogen and $NR_7R_8-$ in which $R_7$ and $R_8$ are each hydrogen or alkyl having 1 to 4 carbon atoms, and together with the nitrogen atom $R_7$ and $R_8$ form a member selected from the group consisting of a 5 to 6 membered heterocyclic ring optionally containing an additional nitrogen atom or oxygen atom, and wherein $R_1$ and $R_2$, or $R_3$ and $R_4$, or $R_5$ and $R_6$, together with the nitrogen atom form a five to six membered heterocyclic ring optionally containing another nitrogen or oxygen atom in the ring, or (B) a water-soluble acid addition salt of (A), or a mixture of said tetraaminopyrimidines, and, as coupler, a mono- and/or di-alkyl-m-dihydroxybenzene, wherein the alkyl radical has 1–4 carbon atoms, or a mixture of said m-dihydroxybenzenes, said developer and said coupler being present in the molar range of about 2:1 to 1:2.

2. The composition of claim 1, wherein the coupler is a mono- and/or di-methyl-m-dihydroxybenzene.

3. The composition of claim 1, wherein the developer is a mixture of the tetraaminopyrimidines.

4. The composition of claim 1, wherein the coupler is a mixture of the mono- and/or di-alkyl-m-dihydroxybenzenes.

5. The composition of claim 1, wherein the developer is a mixture of the tetraaminopyrimidines and the coupler is a mixture of the mono- and/or di-alkyl-m-dihydroxybenzenes.

6. The composition of claim 1 which additionally contains conventional additives selected from the group consisting of conventional developers, conventional couplers, and, optionally, conventional directly absorbing dyes.

7. The composition of claim 1 wherein in the developer $R_1$, $R_2$, $R_3$, $R_4$, $R_5$ and $R_6$ are each selected from the group consisting of hydrogen, methyl, ethyl, isopropyl, n-propyl, butyl, phenyl, benzyl, benzylidene and $-(CH_2)_n-X$, and wherein $R_1$ and $R_2$, or $R_3$ and $R_4$, or $R_5$ and $R_6$, together with the nitrogen atom form a substituent selected from the group consisting of piperidino and morpholino; and wherein n is 1, 2 or 3 and X is selected from the group consisting of hydroxyl, halogen and $-NR_7R_8$ in which $R_7$ and $R_8$ are each hydrogen or alkyl having 1 to 4 carbon atoms.

8. The composition of claim 1 wherein the coupler is a monoalkyl-m-dihydroxybenzene.

9. The composition of claim 8 wherein the coupler is a monomethyl-m-dihydroxybenzene.

10. The composition of claim 1 wherein the coupler is a dialkyl-m-dihydroxybenzene.

11. The composition of claim 10 wherein the coupler is a dimethyl-m-dihydroxybenzene.

12. The composition of claim 1 wherein the developer is selected from the group consisting of 2,4,5,6-tetraaminopyrimidine, 2-methylamino-4,5,6-triaminopyrimidine, 2-dimethylamino-4,5,6-triaminopyrimidine, 2,6-bis-dimethylamino-4,5-diaminopyrimidine, 4-piperidino-2,5,6-triaminopyrimidine and 2-morpholino-4,5,6-triaminopyrimidine and the water-soluble acid addition salts of the above developers, and the coupler is selected from the group consisting of 2,6-dihydroxytoluene, 3,5,-dihydroxytoluene, 2,4-dihydroxytoluene, 2,6-dihydroxyethylbenzene and 4,5-dimethyl-1,3-dihydroxybenzene.

13. An aqueous preparation of the developer-coupler type for the dyeing of hair, consisting essentially of 0.2% to 5% by weight of the developer-coupler combination of claim 1; from 0% to 5% by weight of at least one direct dyestuff; from 0% to 30% by weight of a surfactant; 0% to 25% by weight of a thickener; and the remainder water.

14. The preparation of claim 13 which contains 1% to 3% by weight of the developer-coupler combination.

15. A process for the dyeing of hair comprising applying to said hair, at temperatures ranging substantially from 15° C. to 40° C. for a time sufficient to effect dyeing through oxidation, an effective amount of the developer-coupler composition according to claim 1 in an aqueous medium.

16. The process for the dyeing of hair of claim 15 wherein the oxidation is also effected by the action of a chemical oxidizing agent.

* * * * *